US008082794B2

(12) United States Patent
Aoki et al.

(10) Patent No.: US 8,082,794 B2
(45) Date of Patent: Dec. 27, 2011

(54) ULTRASONIC PROBE AND PIEZOELECTRIC TRANSDUCER

(75) Inventors: Minoru Aoki, Nasushiobara (JP); Hiroyuki Shikata, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 567 days.

(21) Appl. No.: 12/240,221

(22) Filed: Sep. 29, 2008

(65) Prior Publication Data

US 2009/0088643 A1 Apr. 2, 2009

(30) Foreign Application Priority Data

Oct. 2, 2007 (JP) ................................ 2007-258899

(51) Int. Cl.
*H04R 17/00* (2006.01)
*H01L 41/04* (2006.01)
*H01L 41/047* (2006.01)
*A61B 8/04* (2006.01)

(52) U.S. Cl. ............ 73/642; 73/632; 310/342; 600/459

(58) Field of Classification Search .................... 73/642, 73/632, 661; 310/334–337, 387; 600/459
See application file for complete search history.

(56) References Cited

U.S. PATENT DOCUMENTS 4,571,520 A * 2/1986 Saito et al. .................... 310/327
4,992,989 A * 2/1991 Watanabe et al. ................ 367/7
5,274,296 A * 12/1993 Hiki et al. ..................... 310/327
5,434,827 A * 7/1995 Bolorforosh .................. 367/140
5,886,454 A * 3/1999 Ito et al. ........................ 310/322
5,974,884 A * 11/1999 Sano et al. ...................... 73/589
6,799,461 B2 * 10/2004 Fujimoto et al. ........... 73/504.16
6,904,802 B2 * 6/2005 Fujimoto et al. ........... 73/504.16
6,951,135 B2 * 10/2005 Lee et al. ........................ 73/661
7,348,712 B2 * 3/2008 Ogawa et al. ................. 310/334

FOREIGN PATENT DOCUMENTS

JP 2003-9288 1/2003
JP 2005-328507 11/2005

OTHER PUBLICATIONS

U.S. Appl. No. 11/860,799, filed Sep. 25, 2007, Takashi Takeuchi, et al.

* cited by examiner

*Primary Examiner* — J M Saint Surin
(74) *Attorney, Agent, or Firm* — Oblon, Spivak, McClelland, Maier & Neustadt, L.L.P.

(57) ABSTRACT

A ultrasonic probe has a plurality of piezoelectric transducers arranged in the array direction. Each piezoelectric transducer has a piezoelectric element which vibrates in the thickness direction. A signal electrode is formed on the lower surface of the piezoelectric element. An earth electrode is formed on the upper surface of the piezoelectric element. Inside the piezoelectric element, a plurality of non-piezoelectric elements are arranged along the lens direction. Each non-piezoelectric element does not come in contact with the signal electrode and the earth electrode.

8 Claims, 7 Drawing Sheets

D=d1+d2+d3, D=1

- Conventional example (d1 : d2 : d3=0,5 : 0,5 : 0 )
- 14A(d1 : d2 : d3=0,25 : 0,5 : 0,25 )
- 14B(d1 : d2 : d3=0,375 : 0,25 : 0,375 )
- 14C(d1 : d2 : d3=0,4375 : 0,125 : 0,4375 )

ULTRASONIC PROBE AND PIEZOELECTRIC TRANSDUCER

CROSS-REFERENCE TO RELATED APPLICATIONS

This application is based upon and claims the benefit of priority from prior Japanese Patent Application No. 2007-258899, filed Oct. 2, 2007, the entire contents of which are incorporated herein by reference.

BACKGROUND OF THE INVENTION

1. Field of the Invention

The present invention relates to an ultrasonic probe and a piezoelectric transducer that generate ultrasonic waves with transmission intensity weighted.

2. Description of the Related Art

There is a ultrasonic probe which has a plurality of piezoelectric transducers arranged in an array direction. In the linear array ultrasonic probe, when a drive signal is applied to the respective piezoelectric transducers, side lobes in acoustic fields in a lens direction cause problems or the acoustic fields in the lens direction are made non-uniform. Therefore, as a technique to reduce side lobes or to make acoustic fields uniform, weighting the ultrasonic waves in the lens direction is conducted to change the intensity distribution of ultrasonic waves transmitted and received to/from a piezoelectric transducer.

As a technique for weighting in this way, there is a method for achieving desired weighting on the ultrasonic wave intensity in the lens direction by disposing the piezoelectric transducers and grooves for dividing the piezoelectric transducers alternately at predetermined intervals (for example, see Jpn. Pat. Appln. KOKAI Publication No. 2003-9288).

As another technique for weighting, there is a method of forming grooves in the lens direction which are arranged on the top surface or bottom surface or both, of piezoelectric transducers at the depth and intervals in accordance with weighting and at the same time which do not divide the piezoelectric transducers (for example, see Jpn. Pat. Appln. KOKAI Publication No. 2005-328507).

However, the technique stipulated in Jpn. Pat. Appln. KOKAI Publication No. 2003-9288 deals with a structure to completely divide the piezoelectric transducer by grooves (so-called composite structure), and therefore, it is difficult to manufacture an ultrasonic probe. In addition, electrodes must be formed on the resin material filled in grooves, but adhesion of electrodes to the resin material is low and the low reliability of an ultrasonic probe results.

In addition, in the technique stipulated in Jpn. Pat. Appln. KOKAI Publication No. 2005-328507, the weighted intensity depends also on the groove depth. That is, in order to obtain still intensified weighting, still deeper grooves are required. When deep grooves are formed, mechanical strength of piezoelectric transducers is lowered. In addition, in this technique, a plurality of piezoelectric transducer pieces are formed by a plurality of grooves. In this kind of structure, it is important to definitely connect an electrode to each one of the piezoelectric transducer pieces. However, it is difficult to connect electrodes to a plurality of piezoelectric transducer pieces with high reliability by pressure-bonding piezoelectric transducer pieces having high rigidity to acoustic matching layers (or flexible PC boards).

BRIEF SUMMARY OF THE INVENTION

It is an object of the present invention to provide an ultrasonic probe and a piezoelectric transducer that can improve the reliability of electrode connections and improve the yield.

An ultrasonic probe according to a first aspect of the present invention comprises: a plurality of piezoelectric elements which vibrate in a first direction and are arranged along a second direction substantially orthogonal to the first direction; a pair of electrodes formed on each of said plurality of piezoelectric elements; and a plurality of non-piezoelectric elements arranged inside each of said plurality of piezoelectric elements along a third direction substantially orthogonal to the first and second directions.

A piezoelectric transducer according to a second aspect of the present invention comprises: a piezoelectric element which vibrates in a first direction; a pair of electrodes formed on the piezoelectric element; and a plurality of non-piezoelectric elements arranged inside the piezoelectric element along a second direction orthogonal to the first direction.

An ultrasonic probe according to a third aspect of the present invention comprises: an ultrasonic probe comprising: a plurality of piezoelectric elements; a first electrode formed on a first surface of each of the piezoelectric elements; a second electrode formed on a second surface of each of the piezoelectric elements, the second surface being opposite to the first surface; and a plurality of predetermined members buried in an area between the first surface and the second surface of each of the piezoelectric elements.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
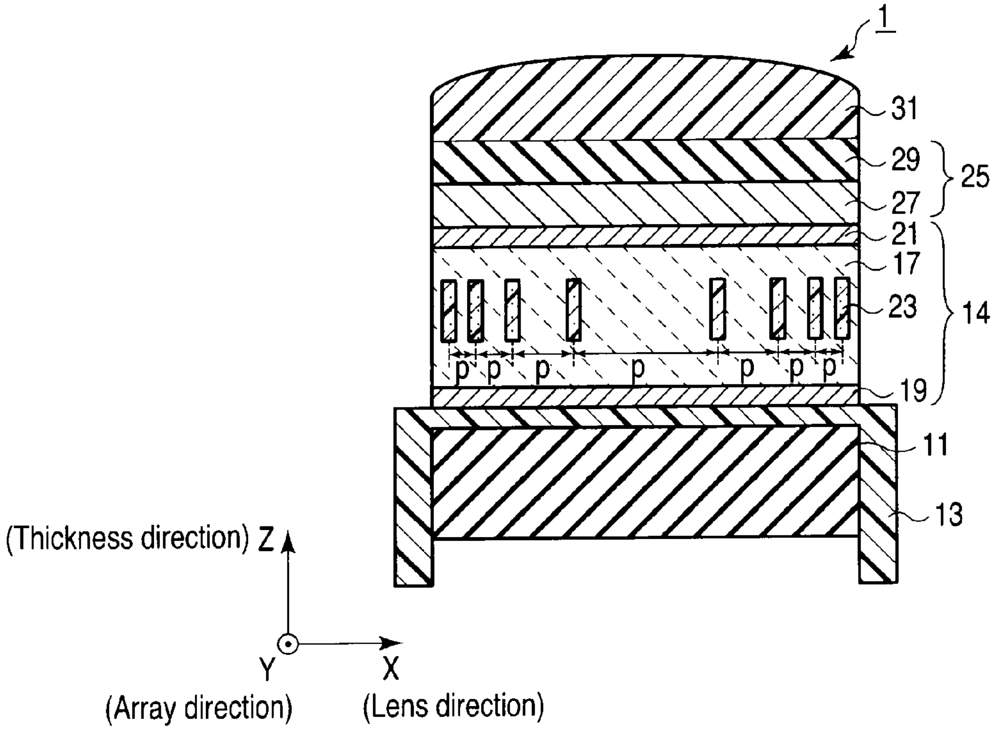
FIG. 1 is a cross-sectional view showing structure of an ultrasonic probe according to an embodiment of the present invention.

Referring now to the drawings, ultrasonic probes and piezoelectric transducers according to embodiments of the present invention will be described.

FIG. 1 is a cross-sectional view showing structure of an ultrasonic probe 1 according to one embodiment of the present invention. As shown in FIG. 1, the ultrasonic probe 1 includes a backing material 11 as a ultrasonic wave absorbing material. The backing material 11 is formed into a rectangular block shape. At the upper surface of the backing material 11, a plurality of piezoelectric transducers 14 are arranged through a flexible PC board (hereinafter called FPC) 13.

Figure 2:
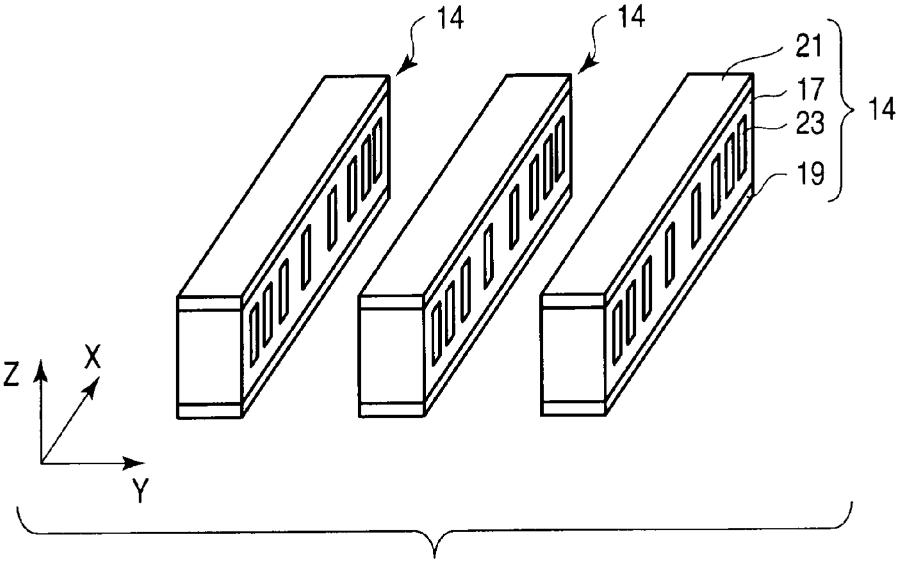
FIG. 2 is a perspective view showing structure of a piezoelectric transducer of FIG. 1.

The plurality of piezoelectric transducers 14 are arranged in one line with predetermined intervals provided with respect to the direction Y perpendicular to the paper surface of FIG. 1 (array direction) as shown in FIG. 2. As shown in FIG. 2, the piezoelectric transducer 14 and the ultrasonic probe 1 are of a so-called linear array type. Each piezoelectric transducer 14 includes a piezoelectric element 17 that vibrates in a direction substantially orthogonal to the array direction Y (hereinafter called the thickness direction), a signal electrode 19 formed on a flat and uniform lower surface of the piezoelectric element 17, and a earth electrode 21 formed on a flat and uniform upper surface of the piezoelectric element 17.

Inside the piezoelectric element 17, a plurality of non-piezoelectric elements 23 are arranged at a plurality of varying pitch intervals (center-to-center distance of adjacent non-piezoelectric elements 23) p along a direction substantially orthogonal to the array direction Y and the thickness direction Z (hereinafter called the lens direction). The non-piezoelectric elements 23 have substantially strip shapes and pass through the piezoelectric element 17 in the array direction Y. The pitch intervals p of the non-piezoelectric elements 23 are based on weighting of the ultrasonic wave intensity related to the lens direction. In addition, the length concerning the thickness direction Z of the non-piezoelectric elements 23 is based on the weighting. By weighting, the piezoelectric transducer 14 can transmit uniform ultrasonic waves with respect to the lens direction as compared to the case of equal pitch intervals. The plurality of non-piezoelectric elements 23 do not reach either of both surfaces (both surfaces with electrodes 19 and 21 formed) of the piezoelectric element 17 substantially orthogonal to the thickness direction Z. The non-piezoelectric elements 23 are buried in an area between the both surfaces of the piezoelectric element 17. Although the non-piezoelectric elements 23 are typically formed by hardened adhesives of composite material, etc. of epoxy resin or epoxy resin mixed with fillers, any adhesive can be employed for the non-piezoelectric elements 23 as long as no piezoelectric properties are exhibited. For the material of the piezoelectric element 17, two-component system or three-component system piezoelectric ceramics or piezoelectric monocrystals are used. The detail concerning the structure of the piezoelectric transducer 14 will be discussed later.

Each signal electrode 19 is formed by metal plating by silver, gold, etc. or sputtering. Each signal electrode 19 is electrically connected to each wiring disposed to the FPC 13, one by one. As a result, drive signals are applied individually to the plurality of piezoelectric transducers 14.

The FPC 13 is disposed between the backing material 11 and the piezoelectric transducer 14 as described above. The FPC 13 is composed of a plurality of wirings for supplying electric power to a plurality of signal electrodes 19, flexible substrates, etc. The signal electrodes 19 and wirings are electrically connected. Through this wiring, a predetermined voltage is applied to the signal electrode 19 from an ultrasonic diagnostic apparatus body not shown in the figure.

To the upper surface of the piezoelectric transducers 14, a plurality of acoustic matching layers 25 are disposed. The acoustic matching layers 25 play a role to suppress reflection of ultrasonic waves arising from a difference between acoustic impedance of a patient and acoustic impedance of the piezoelectric transducers 14. The acoustic matching layer 25 is provided with a first acoustic matching layer 27 and a second acoustic matching layer 29. By the first acoustic matching layer 27 and the second acoustic matching layer 29, the acoustic impedance is changed stepwise from the piezoelectric transducer 14 to a patient. The first acoustic matching layer 27 is formed of a conductive material. The lower surface of the first acoustic matching layer 27 is electrically connected to the piezoelectric transducer 14 through the earth electrode 21. The upper surface of the first acoustic matching layer 27 is joined with the second acoustic matching layer 29. The second acoustic matching layer 29 is formed of an insulating material. Note that, the acoustic matching layer 25 is composed of two layers of acoustic matching layers, but it may be composed of one layer or three layers, or more layers of acoustic matching layers.

An acoustic lens 31 is mounted on the upper surface of a plurality of acoustic matching layers 25. The acoustic lens 31 is a lens made of silicone rubber, etc., which has the acoustic impedance close to a living body. The acoustic lens 31 focuses ultrasonic waves in the lens direction and improves resolution.

Figure 3:
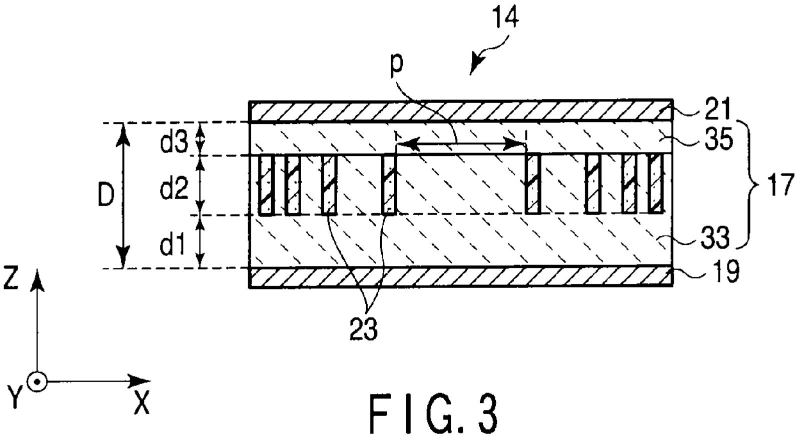
FIG. 3 is a cross-sectional view showing structure of the piezoelectric transducer of FIG. 1.

Next discussion will be made on the specific structure of the piezoelectric transducer 14. As shown in FIG. 3, the piezoelectric element 17 of the piezoelectric transducer 14 is composed by joining a first piezoelectric element portion 33 and a second piezoelectric element portion 35 by lamination adhesives, etc.

The first piezoelectric element portion 33 includes a plurality of non-piezoelectric elements 23 which are filled, respectively, in a plurality of grooves formed at pitch intervals p based on weighting of ultrasonic intensity along the lens direction X. The plurality of pitch intervals p are increased as they come closer to the center of the lens direction X due to weighting. Each pitch interval p is determined on the basis of sine functions, Gaussian functions, and other functions. On the lower surface of the first piezoelectric element portion 33, the signal electrode 19 is formed by sputtering, etc. Now, let d1 denote the thickness from the bottom end of the non-piezoelectric element 23 concerning the thickness direction Z to the signal electrode 19 and d2 denote the thickness from the upper end to the lower end of the non-piezoelectric element 23. The thickness d2 is determined in accordance with the desired ultrasonic intensity. In this event, assume that the thickness D2 of the non-piezoelectric element 23 is constant. The second piezoelectric element portion 35 is a plate type piezoelectric element. On the upper surface of the second piezoelectric element portion 35, the earth electrode 21 is formed by sputtering, etc.

When drive signals are applied from an ultrasonic diagnostic apparatus body to the signal electrode 19, the first piezoelectric element portion 33 and the second piezoelectric element portion 35 vibrate in an integrated manner. Consequently, the basic resonance characteristics of the piezoelectric transducer 14 are determined on the basis of the thickness d1+d2 combining the overall thickness of the first piezoelectric portion element 33 and the thickness d3 of the second piezoelectric element portion 35 (length from the upper end of the non-piezoelectric element 23 to the earth electrode 21), that is, thickness D (D=d1+d+d3) of the piezoelectric element 17. In addition, the signal electrode 19 and the earth electrode 21 are formed on flat and uniform end surfaces of the first and second piezoelectric element portions 33 and 35, and therefore, as compared to conventional examples (Jpn. Pat. Appln. KOKAI Publication Nos. 2003-9288 and 2005-328507), they have high reliability in electrode connection.

Figure 4:
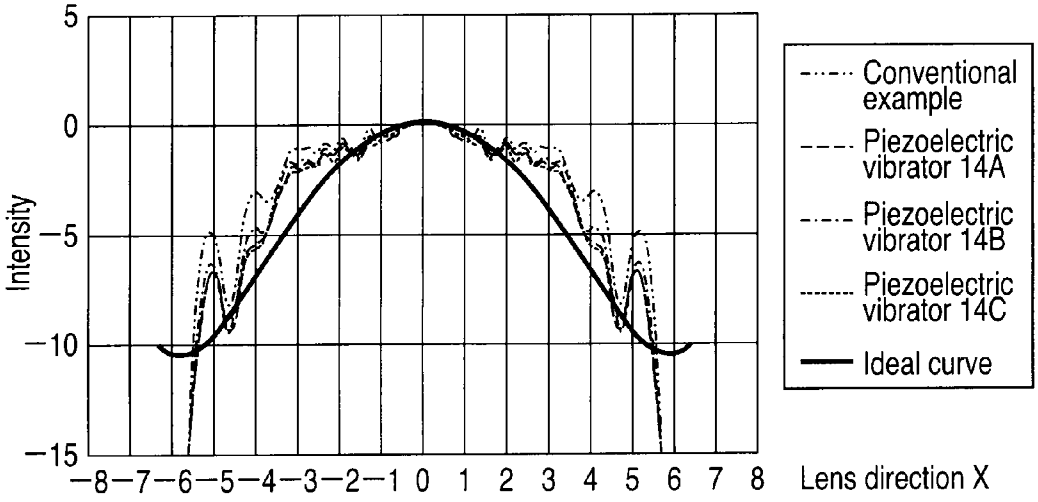
FIG. 4 is a diagram showing simulation results for comparing sound pressure distribution of ultrasonic waves generated from three types of ultrasonic probes according to the present embodiment and conventional ultrasonic probe.

Next description will be made on the sound pressure distribution by the ultrasonic probe 1. FIG. 4 shows simulation results obtained when sound pressure distributions of ultrasonic waves generated from a conventional ultrasonic probe (described in Jpn. Pat. Appln. KOKAI Publication No. 2005-328507) and three types of ultrasonic probes according to the present embodiment are compared. The three types of ultrasonic probes according to the present embodiment differ in the structure of the piezoelectric transducer only, and are called piezoelectric transducer 14A, piezoelectric transducer 14B, and piezoelectric transducer 14C, respectively. FIG. 4 is a graph with the ordinate defined as the intensity of ultrasonic waves and the abscissa defined as the position in the lens direction X. X=0 is the center of the piezoelectric transducer 14 relative to the lens direction X. In this simulation, computation was conducted with the center frequency set to about 2.5 MHz for both conventional case and the present embodiment. Thicknesses D of the piezoelectric elements of four piezoelectric transducers used for the simulation are all equal. The solid line of the graph indicates an ideal curve of the ultrasonic intensity distribution. Meanwhile, in FIG. 17, a structure of a piezoelectric transducer 100 of a conventional (described in Patent Document 2) ultrasonic probe is shown.

Figure 17:
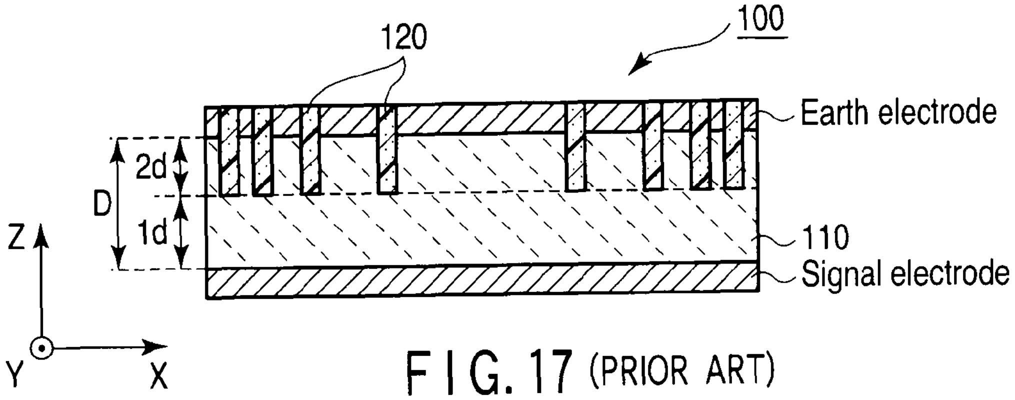
FIG. 17 (PRIOR ART)
FIG. 17 is a cross-sectional view showing structure of a conventional piezoelectric transducer.

The piezoelectric transducer 100 in the "conventional example" of FIG. 17 has a non-piezoelectric element 120 having half the length of the thickness D of the piezoelectric element 110. Assume that the thickness D of the piezoelectric element 110 is 1; then, d1=0.5, d2=0.5, and d3=0. For the "piezoelectric transducer 14A," the ratio of the length d2 of the non-piezoelectric element 23 was set to half the thickness D of the piezoelectric element 17. That is, in the "piezoelectric transducer 14A," d1=0.25, d2=0.5, and d3=0.25. For the "piezoelectric transducer 14B," the ratio of the length d2 of the non-piezoelectric element 23 was set to one-fourth of the piezoelectric element 17. That is, in the "piezoelectric transducer 14B," d1=0.375, d2=0.25, and d3=0.375. For the "piezoelectric transducer 14C," the ratio of the length d2 of the non-piezoelectric element 23 was set to one-eighth of the piezoelectric element 17. That is, in the "piezoelectric transducer 14C," d1=0.4375, d2=0.125, and d3=0.4375.

As shown in FIG. 4, when the "conventional example" and "piezoelectric transducer 14A" are compared, in which the length d2 of the non-piezoelectric element is the same, the effect of weighting is exhibited more strongly in the "piezoelectric transducer 14A." This means that more uniform acoustic field can be obtained with respect to the lens direction. This result indicates that when a non-piezoelectric element (groove) is formed in the length of the same ratio, stronger weighting effect can be obtained in the piezoelectric transducer 14 according to the present embodiment than in the conventional example.

Next, when the "piezoelectric transducer 14A," "piezoelectric transducer 14B," and "piezoelectric transducer 14C" are compared, it is obvious that the weighting effect varies in accordance with the length d2 of the non-piezoelectric element 23. The "conventional example" and the "piezoelectric transducer 14B" have substantially the same weighting effect but when the ratio of the length d2 of the non-piezoelectric element (groove) is compared, the "piezoelectric transducer 14B" is half the "conventional example."

The foregoing simulation results indicate that stronger weighting effect can be obtained with shorter length d2 of the non-piezoelectric element 23 as compared to the conventional example.

Next, referring to FIGS. 5 to 14, one example of a manufacturing process of the piezoelectric transducer 14 and the ultrasonic probe 1 will be explained. First of all, after understanding the desired piezoelectric characteristics of the piezoelectric transducer 14, the thickness D of the piezoelectric element 17, thickness d1+d2 of the first piezoelectric element portion 33, and the thickness d3 of the second piezoelectric element portion 35 are determined. In general, the higher the center frequency, the thinner the thickness D of the piezoelectric element 17. In addition, the pitch intervals of the groove (that is non-piezoelectric element) 23 for weighing the desired ultrasonic waves are determined.

Figure 5:
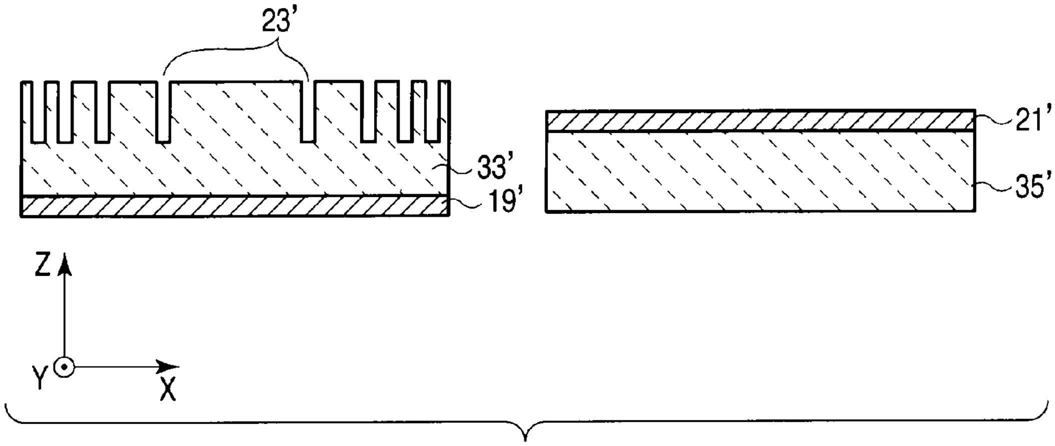
FIG. 5 shows a manufacturing process S1 of the ultrasonic probe and the piezoelectric transducer of FIG. 1.

As shown in FIG. 5 (manufacturing process S1), a first piezoelectric block (piezoelectric material) 33' with a plurality of grooves 23' formed and a first electrode 19' formed on a lower surface by sputtering, etc. is formed. The grooves 23' are formed on the upper surface of the first piezoelectric block 33' by dicing, etc. The pitch intervals p between the grooves 23' are determined on the basis of the weighting of ultrasonic waves as described above. In addition, a second piezoelectric block (piezoelectric material) 35' with a second electrode 21' formed on the upper surface is formed by sputtering, etc.

Figure 6:
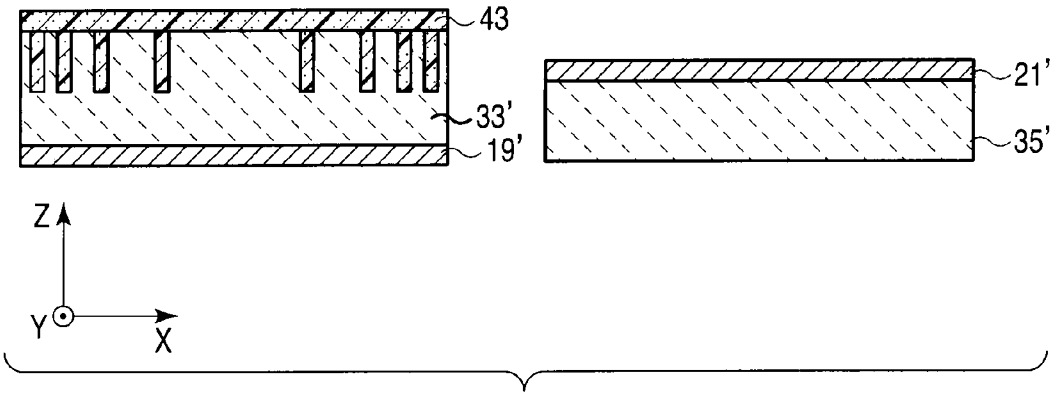
FIG. 6 shows a manufacturing process S2 of the ultrasonic probe and the piezoelectric transducer of FIG. 1.
Figure 7:
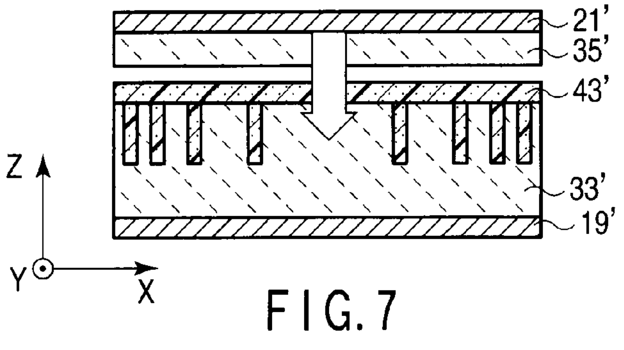
FIG. 7 shows a manufacturing process S3 of the ultrasonic probe and the piezoelectric transducer of FIG. 1.

Then, as shown in FIG. 6 (manufacturing process S2), a plurality of grooves 23' of the first piezoelectric block 33' are filled with adhesives. By filling composite material with a granular filler mixed as adhesives, grinding, cutting, dicing, and other processing become easier as compared to with a filler made of resin material only. For the filler, alumina powders, zinc oxide powders, aluminum nitride powders, and other nonconductive members are used. When the grooves 23' are filled with adhesives 43, as shown in FIG. 7 (manufacturing process S3), the upper surface of the first piezoelectric block 33' and the lower surface of the second piezoelectric block 35' are pressure-bonded. The thickness of the adhesives after pressure-bonding becomes several μm. By the bonding, the groove 23' becomes the non-piezoelectric element 23'.

Figure 8:
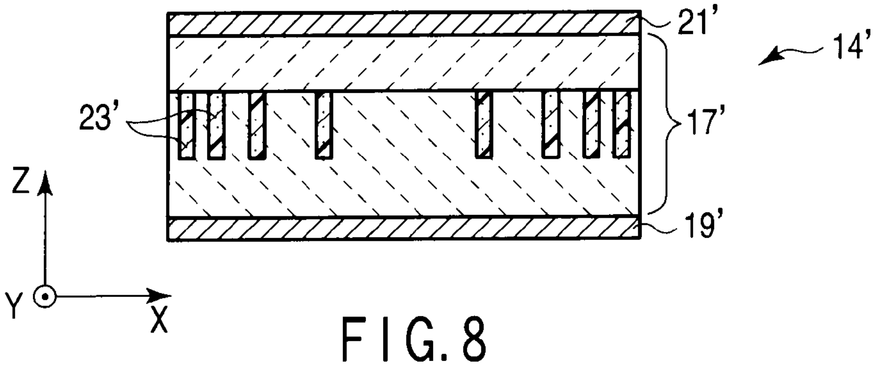
FIG. 8 shows a manufacturing process S4 of the ultrasonic probe and the piezoelectric transducer of FIG. 1.

As shown in FIG. 8 (manufacturing process S4), when the adhesives become hardened, the first piezoelectric block 33' and the second piezoelectric block 35' are integrated and a piezoelectric transducer 14' is formed. Thereafter, predetermined voltage is applied (polarized) to a first electrode 19' and a second electrode 21'. The polarization direction is the same as the thickness direction.

Figure 9:
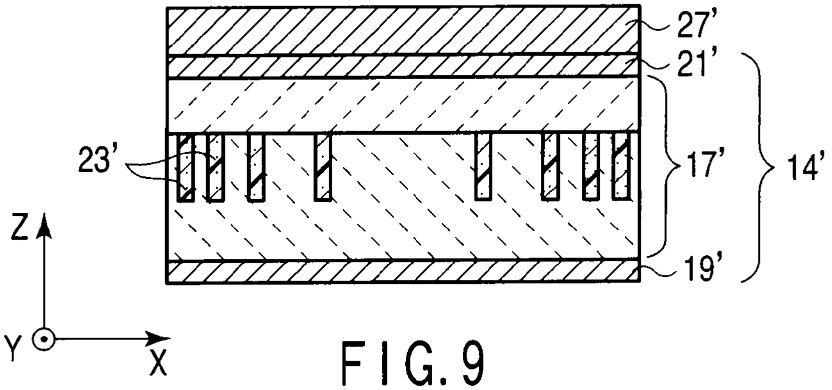
FIG. 9 shows a manufacturing process S5 of the ultrasonic probe and the piezoelectric transducer of FIG. 1.
Figure 10:
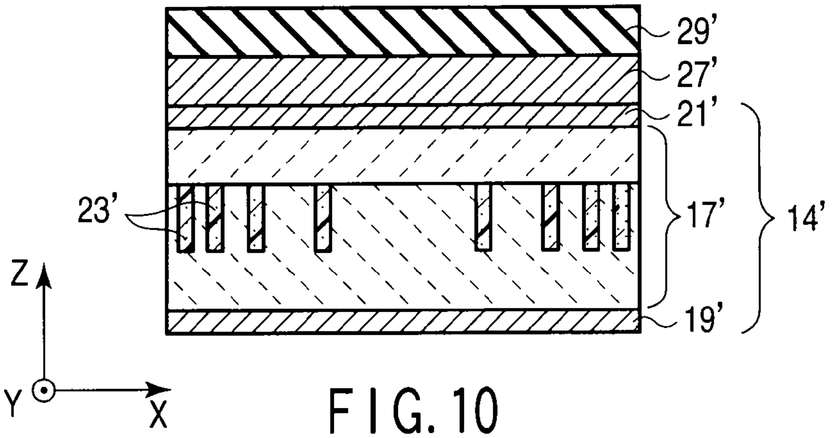
FIG. 10 shows a manufacturing process S6 of the ultrasonic probe and the piezoelectric transducer of FIG. 1.
Figure 11:
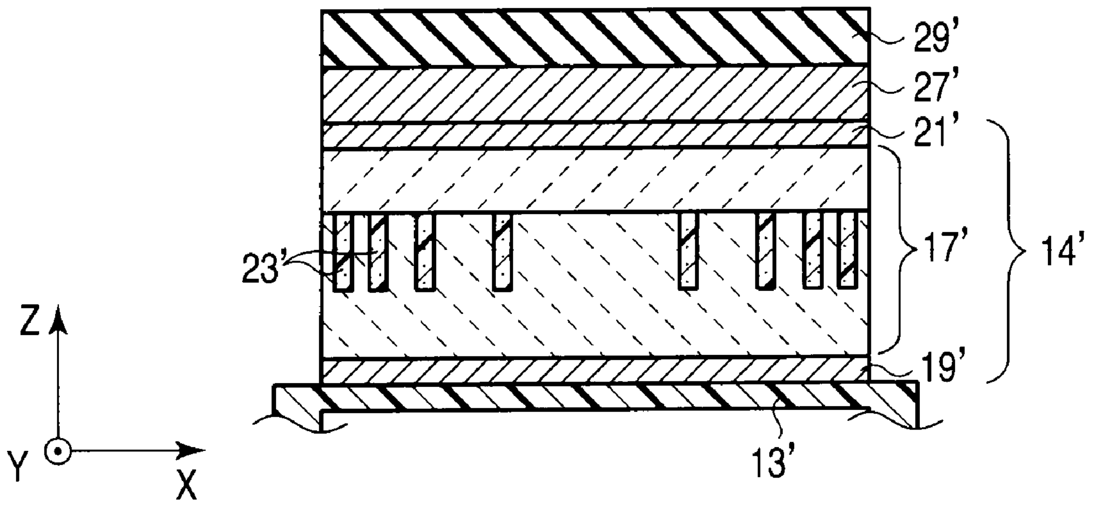
FIG. 11 shows a manufacturing process S7 of the ultrasonic probe and the piezoelectric transducer of FIG. 1.

Next, as shown in FIG. 9 (manufacturing process S5), a first acoustic matching material 27', etc. are bonded to the upper part of the piezoelectric transducer 14' by adhesives, etc., and the first acoustic matching material 27' is electrically joined onto the second electrode 21'. Then, as shown in FIG. 10 (manufacturing process S6), a second acoustic matching material 29' is joined to the upper part of the first acoustic matching material 27'. Then, as shown in FIG. 11 (manufacturing process S7), a flexible wiring board 13' is joined to the first electrode 19' and the signal wiring and the first electrode 19' are electrically connected.

Figure 12:
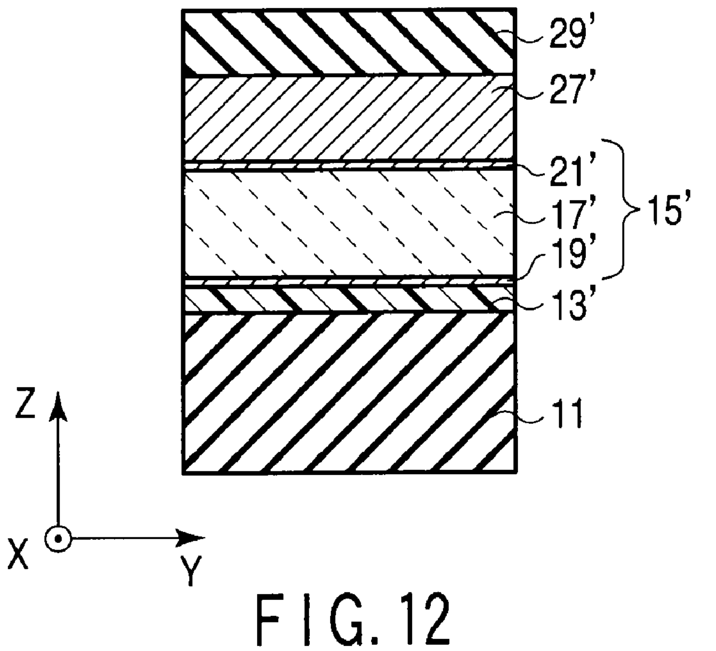
FIG. 12 shows a manufacturing process S8 of the ultrasonic probe and the piezoelectric transducer of FIG. 1.
Figure 13:
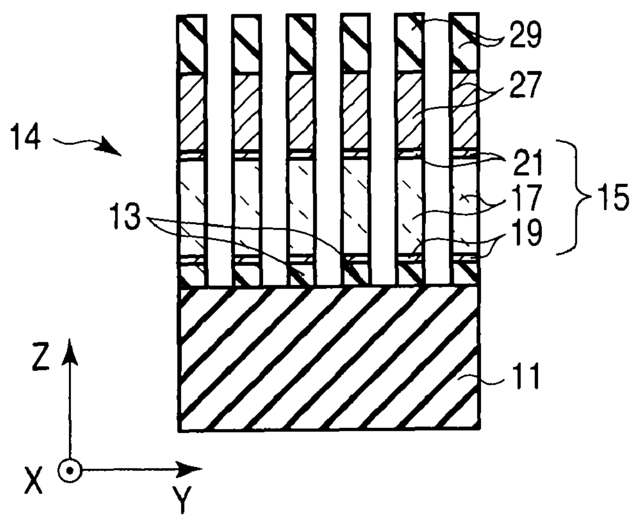
FIG. 13 shows a manufacturing process S9 of the ultrasonic probe and the piezoelectric transducer of FIG. 1.

Thereafter, as shown in FIG. 12 (manufacturing process S8), the backing material 11 is joined to the lower part of the flexible wiring board 13' joined to the piezoelectric transducer 14'. Then, as shown in FIG. 13 (manufacturing process S9), the piezoelectric transducer 14', first acoustic matching material 27', second acoustic matching material 29', first electrode 19', second electrode 21', and flexible wiring board 13 are diced from the second acoustic matching material 29' along the array direction Y by a blade. By this dicing, the piezoelectric transducer 14', first acoustic matching material 27', second acoustic matching material 29', first electrode 19', second electrode 21', and flexible wiring board 13' are separated into a plurality of piezoelectric transducers 14, first acoustic matching layers 27, second acoustic matching layers 29, signal electrodes 19, and earth electrodes 21 arranged at predetermined intervals in the array direction Y, respectively. By dicing, between a plurality of piezoelectric transducers 14, first acoustic matching layers 27, second acoustic matching layers 29, signal electrodes 19, and earth electrodes 21, a plurality of clearances are formed.

Figure 14:
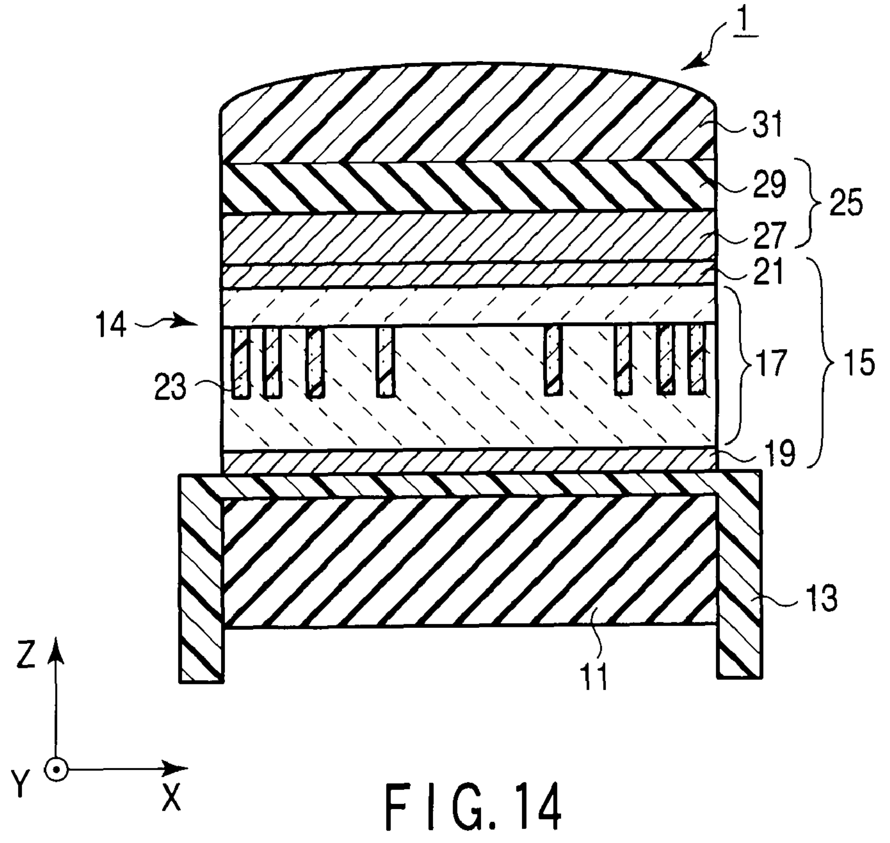
FIG. 14 shows a manufacturing process S10 of the ultrasonic probe and the piezoelectric transducer of FIG. 1.

Next, as shown in FIG. 14 (manufacturing process S10), the acoustic lens 31 is joined so as to cover the whole upper part of the plurality of second acoustic matching layers 29, thereby completing the ultrasonic probe 1.

Incidentally, the piezoelectric transducer 14' which is manufactured in the manufacturing process S4 (FIG. 5) and is not diced with respect to the array direction X is prepared in advance, and using this piezoelectric transducer 14', the ultrasonic probe 1 may be fabricated by manufacturing processes S5 through S10.

By the above-mentioned configuration, each piezoelectric element 17 is provided, in its inside, with a plurality of substantially strip-shape non-piezoelectric elements 23 disposed along the lens direction. Consequently, the piezoelectric element 17 can have two flat surfaces which substantially cross at right angles with the thickness direction Z, and which cannot be realized in the conventional example in which weighting is performed to change intensity distribution of ultrasonic waves. Because the electrodes are formed on the two flat surfaces, the electrode adhesion strength of the piezoelectric element 17 can be increased. In addition, the piezoelectric transducer 14 can be weighted as desired by the non-piezoelectric elements (grooves) 23 which are shorter than conventional ones, and therefore, the mechanical strength of the ultrasonic probe 1 and the piezoelectric transducer is improved. Consequently, according to the present embodiment, both the reliability of electrode formation and the yield can be improved.

Incidentally, the grooves 23 may not be filled with anything, though it has been stated that the grooves are filled with adhesives, etc.

Figure 15:
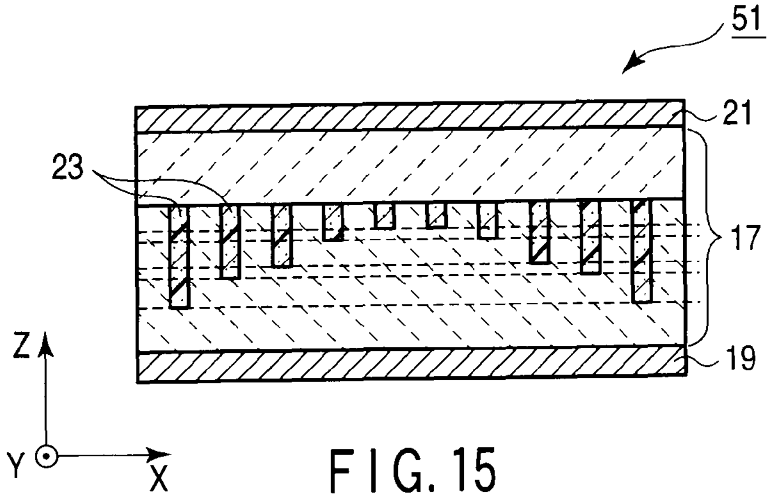
FIG. 15 is a cross-sectional view showing structure of another piezoelectric transducer according to the present embodiment.

In addition, the length d2 and the shape of the non-piezoelectric element 23 are not limited to the above-mentioned embodiments only. For example, as is the case of a piezoelectric transducer 51 shown in FIG. 15, the plurality of non-piezoelectric elements 23 may be arranged at substantially the same pitch intervals and the length of the non-piezoelectric elements 23 may be formed to be gradually increased as they go to both surfaces in the lens direction X.

Figure 16:
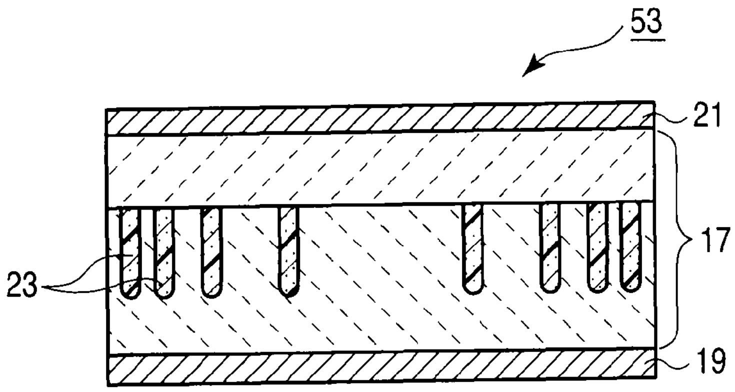
FIG. 16 is a cross-sectional view showing structure of another piezoelectric transducer different from FIG. 14 according to the present embodiment.

Furthermore, as is the case of a piezoelectric transducer 53 shown in FIG. 16, the shape of the bottom of the non-piezoelectric element 23 is not limited to a rectangle. For example, the shape of the bottom of the non-piezoelectric element 23 may be a circular arc. By making the bottom of the non-piezoelectric element 23 be a circular arc, it is possible to avoid concentration of stress against external force at the angular part arising from the rectangular structure. Consequently, the piezoelectric transducer 53 has the mechanical strength improved as compared to the piezoelectric transducer 14 and the piezoelectric transducer 51. Incidentally, the shape of the bottom of the non-piezoelectric element 23 is determined depending on the shape of a blade used when the groove 23' is formed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe comprising:

a plurality of piezoelectric elements which vibrate in a first direction and are arranged along a second direction substantially orthogonal to the first direction;

a pair of electrodes formed on each of said piezoelectric elements; and a plurality of non-piezoelectric elements arranged inside each of said piezoelectric elements along a third direction substantially orthogonal to the first and second directions, wherein each of the non-piezoelectric elements is arranged inside the piezoelectric element so as not to come in contact with said pair of electrodes.

2. The ultrasonic probe according to claim 1, wherein each of the piezoelectric elements comprises:

a first piezoelectric element portion having a first surface and a second surface substantially orthogonal to the first direction, with one of said pair of electrodes formed on the first surface and with a plurality of grooves arranged along the third direction on the second surface; and a second piezoelectric element portion having a third surface and a fourth surface substantially orthogonal to the first direction, with the second surface of the first piezoelectric element portion joined to the third surface and with the other one of said pair of electrodes formed on the fourth surface, and said plurality of non-piezoelectric elements are disposed in said plurality of grooves, respectively.

3. The ultrasonic probe according to claim 1, wherein a length of said each of non-piezoelectric elements according to the first direction and a center-to-center interval of adjacent two non-piezoelectric elements according to the third direction are determined on the basis of weighting to vary an intensity distribution of ultrasonic waves.

4. The ultrasonic probe according to claim 1, wherein each of the non-piezoelectric elements comprises resins.

5. The ultrasonic probe according to claim 1, wherein each of the non-piezoelectric elements comprises a composite material formed by mixing fillers and resins.

6. A piezoelectric transducer comprising:

a piezoelectric element which vibrates in a first direction;

a pair of electrodes formed on the piezoelectric element; and a plurality of non-piezoelectric elements arranged inside the piezoelectric element along a second direction orthogonal to the first direction, wherein each of the non-piezoelectric elements is arranged inside the piezoelectric element so as not to come in contact with said pair of electrodes.

7. The piezoelectric transducer according to claim 6, wherein the piezoelectric element comprises:

a first piezoelectric element portion having a first surface and a second surface substantially orthogonal to the first direction, with one of said pair of electrodes formed on the first surface and with a plurality of grooves arranged along the second direction on the second surface; and a second piezoelectric element portion having a third surface and a fourth surface substantially orthogonal to the first direction, with the second surface of the first piezoelectric element portion joined to the third surface and with the other one of said pair of electrodes formed on the fourth surface, and said plurality of non-piezoelectric elements are disposed in said plurality of grooves, respectively.

8. The piezoelectric transducer according to claim 6, wherein a length of said each of non-piezoelectric elements according to the first direction and a center-to-center interval of adjacent two non-piezoelectric elements according to the second direction are determined on the basis of weighting to vary an intensity distribution of ultrasonic waves.

* * * * *